US006901215B2

United States Patent
He et al.

(10) Patent No.: US 6,901,215 B2
(45) Date of Patent: May 31, 2005

(54) VAPOR DISPENSING DEVICE HAVING IMPROVED TRANSVERSE LOADING STABILITY

(75) Inventors: Mengtao Pete He, Scottsdale, AZ (US); Carl Triplett, Scottsdale, AZ (US); Mary Conway, Phoenix, AZ (US); David Rinaldis, Longmont, CO (US); Michael Strasser, Lafayette, CA (US); Francis Joseph Mills, IV, Holt, MI (US)

(73) Assignee: The Dial Corporation, Scottsdale, AZ (US)

( * ) Notice: Subject to any disclaimer, the term of this patent is extended or adjusted under 35 U.S.C. 154(b) by 0 days.

(21) Appl. No.: 10/640,116

(22) Filed: Aug. 13, 2003

(65) Prior Publication Data

US 2004/0096201 A1 May 20, 2004

Related U.S. Application Data

(63) Continuation-in-part of application No. 10/222,070, filed on Aug. 16, 2002.

(51) Int. Cl.[7] .................................................. F24F 6/00
(52) U.S. Cl. ....................................... 392/392; 392/390
(58) Field of Search ............................... 392/386, 390, 392/392, 394, 395; 239/34, 35, 135, 136; 261/16.65, 141, 142

(56) References Cited

U.S. PATENT DOCUMENTS

| | | |
|---|---|---|
| 1,836,600 A | 12/1931 | Jones |
| 3,262,290 A | 7/1966 | Huber |
| 3,748,438 A | 7/1973 | Costello |
| 3,780,260 A | 12/1973 | Eisner |
| 3,895,928 A | 7/1975 | Gonzalo |
| 3,908,905 A | 9/1975 | Von Philipp et al. |
| 3,923,458 A | 12/1975 | Gonzalo |
| 3,948,445 A | 4/1976 | Andweg |
| 4,017,030 A | 4/1977 | Coplan et al. |
| 4,037,353 A | 7/1977 | Hennart et al. |

(Continued)

FOREIGN PATENT DOCUMENTS

| | | |
|---|---|---|
| DE | 35 35 564 | 5/1986 |
| DE | 41 31 613 | 3/1993 |
| EP | 0 296 807 | 12/1988 |
| EP | 0 669 137 | 8/1995 |
| EP | 0 911 041 | 4/1999 |
| GB | 402507 | 12/1933 |
| GB | 2 356 815 | 6/2001 |
| WO | WO 00 76292 | 12/2000 |
| WO | WO 01 10739 | 2/2001 |
| WO | WO 01/68154 | 9/2001 |
| WO | WO 01/93919 | 12/2001 |

OTHER PUBLICATIONS

PCT International Search Report issued Dec. 17, 2003 for International Application No. PCT/US03/26511, International Filing Date Aug. 26, 2003, 4 pages.

(Continued)

*Primary Examiner*—Sang Paik
(74) *Attorney, Agent, or Firm*—Snell & Wilmer LLP (57) ABSTRACT

A vapor dispensing device having a high transverse loading stability includes a relatively low profile with respect to the supporting wall or electrical receptacle such that the frequency and impact of accidental physical contact with the device are appropriately reduced. To achieve a low profile, the housing of a vapor dispensing device is designed such that the distance from the outlet face of the wall receptacle to a worst-case transverse loading point ($d_L$) is less than the distance from the plug to a worst-case support point ($d_S$).

6 Claims, 7 Drawing Sheets

U.S. PATENT DOCUMENTS

| | | |
|---|---|---|
| 4,084,079 A | 4/1978 | Costello |
| 4,111,655 A | 9/1978 | Quincey |
| 4,123,741 A | 10/1978 | Kiyono et al. |
| 4,165,835 A | 8/1979 | Dearling |
| 4,171,340 A | 10/1979 | Nishimura et al. |
| 4,208,012 A | 6/1980 | Dutcher |
| 4,214,146 A | 7/1980 | Schimanski |
| 4,220,281 A | 9/1980 | Martens, III et al. |
| 4,228,124 A | 10/1980 | Kashihara et al. |
| 4,243,969 A | 1/1981 | Steigerwald et al. |
| 4,293,173 A | 10/1981 | Tricca |
| 4,294,778 A | 10/1981 | DeLuca |
| 4,346,059 A | 8/1982 | Spector |
| 4,391,781 A | 7/1983 | Van Lit |
| 4,408,813 A | 10/1983 | Koehler |
| 4,413,779 A | 11/1983 | Santini |
| 4,415,797 A | 11/1983 | Choustoulakis |
| 4,425,302 A | 1/1984 | Pons Pons |
| 4,467,177 A | 8/1984 | Zobele |
| 4,518,212 A | 5/1985 | Rumble |
| 4,530,556 A | 7/1985 | Bonus |
| 4,537,351 A | 8/1985 | Wilson |
| 4,544,592 A | 10/1985 | Spector |
| 4,549,250 A | 10/1985 | Spector |
| 4,556,539 A | 12/1985 | Spector |
| 4,571,485 A | 2/1986 | Spector |
| 4,574,181 A | 3/1986 | Spector |
| 4,595,564 A | 6/1986 | Spector et al. |
| 4,631,387 A | 12/1986 | Glucksman |
| 4,658,985 A | 4/1987 | Madsen et al. |
| 4,660,764 A | 4/1987 | Joyaux et al. |
| 4,662,679 A | 5/1987 | Franck |
| 4,675,504 A | 6/1987 | Suhajda |
| 4,686,353 A | 8/1987 | Spector |
| 4,695,434 A | 9/1987 | Spector |
| 4,703,155 A | 10/1987 | Suhajda |
| 4,707,336 A | 11/1987 | Jones |
| 4,714,984 A | 12/1987 | Spector |
| 4,718,856 A | 1/1988 | Pinkerton et al. |
| 4,725,712 A | 2/1988 | Schroeder |
| 4,731,520 A | 3/1988 | Glucksman |
| 4,731,522 A | 3/1988 | Manchester |
| 4,732,321 A | 3/1988 | Dolan |
| 4,734,560 A | 3/1988 | Bowen |
| 4,739,928 A | 4/1988 | O'Neil |
| 4,743,406 A | 5/1988 | Steiner et al. |
| 4,753,389 A | 6/1988 | Davis |
| 4,777,345 A | 10/1988 | Manchester |
| 4,780,286 A | 10/1988 | Parent et al. |
| 4,795,883 A | 1/1989 | Glucksman et al. |
| 4,798,935 A | 1/1989 | Pezaris |
| 4,800,239 A | 1/1989 | Hill |
| 4,801,271 A | 1/1989 | Piper |
| 4,804,821 A * | 2/1989 | Glucksman ................ 392/390 |
| 4,808,347 A | 2/1989 | Dawn |
| 4,816,973 A | 3/1989 | Atalla et al. |
| 4,830,791 A | 5/1989 | Muderlak et al. |
| 4,837,421 A | 6/1989 | Luthy |
| 4,849,606 A | 7/1989 | Martens, III et al. |
| 4,853,517 A | 8/1989 | Bowen et al. |
| 4,878,615 A | 11/1989 | Losi |
| 4,886,469 A | 12/1989 | Jseng |
| 4,915,301 A | 4/1990 | Munteanu |
| 4,919,981 A | 4/1990 | Levey et al. |
| 4,931,224 A | 6/1990 | Holzner, Sr. |
| 4,931,258 A | 6/1990 | Zlotnik et al. |
| 4,968,456 A | 11/1990 | Muderlak et al. |
| D315,789 S | 3/1991 | Muderlak |
| 4,998,671 A | 3/1991 | Leifheit |
| 5,004,435 A | 4/1991 | Jammet |
| 5,014,913 A | 5/1991 | Hoyt et al. |
| 5,015,442 A | 5/1991 | Hirai |
| 5,029,729 A | 7/1991 | Madsen et al. |
| 5,038,394 A | 8/1991 | Hasegawa et al. |
| 5,050,798 A | 9/1991 | Sullivan |
| 5,106,317 A | 4/1992 | Taylor |
| 5,111,477 A | 5/1992 | Muderlak |
| 5,115,975 A | 5/1992 | Shilling |
| 5,121,881 A | 6/1992 | Lembeck |
| 5,126,078 A | 6/1992 | Steiner et al. |
| 5,136,684 A | 8/1992 | Lonker et al. |
| 5,147,582 A | 9/1992 | Holzner, Sr. et al. |
| 5,148,984 A | 9/1992 | Bryson, Jr. et al. |
| 5,175,791 A | 12/1992 | Muderlak et al. |
| 5,196,171 A | 3/1993 | Peltier |
| 5,201,025 A | 4/1993 | Landesberg |
| 5,217,696 A | 6/1993 | Wolverton et al. |
| 5,220,636 A | 6/1993 | Chang |
| 5,222,186 A | 6/1993 | Schimanski et al. |
| 5,223,182 A | 6/1993 | Steiner et al. |
| 5,233,680 A | 8/1993 | Fussell |
| 5,239,610 A | 8/1993 | Shao |
| 5,240,426 A | 8/1993 | Barla |
| 5,285,014 A | 2/1994 | Gilchrist |
| 5,290,546 A | 3/1994 | Hasegawa et al. |
| 5,295,845 A | 3/1994 | Changxing |
| 5,314,669 A | 5/1994 | Hamilton |
| 5,320,542 A | 6/1994 | Cheng |
| 5,339,065 A | 8/1994 | Slenker |
| 5,342,584 A | 8/1994 | Fritz et al. |
| 5,373,581 A | 12/1994 | Smith |
| 5,375,728 A | 12/1994 | West |
| 5,376,338 A | 12/1994 | Zlotnik |
| 5,382,410 A | 1/1995 | Peltier |
| D355,251 S | 2/1995 | Paulovich et al. |
| 5,394,506 A | 2/1995 | Stein et al. |
| 5,402,517 A | 3/1995 | Gillett et al. |
| D357,330 S | 4/1995 | Wong et al. |
| 5,431,859 A | 7/1995 | Tobin |
| 5,431,885 A | 7/1995 | Zlotnik et al. |
| 5,445,802 A | 8/1995 | Wendelken |
| 5,465,198 A | 11/1995 | Kellogg |
| 5,480,591 A | 1/1996 | Lagneaux et al. |
| 5,481,442 A | 1/1996 | Wiltshire et al. |
| 5,484,086 A | 1/1996 | Pu |
| 5,498,397 A | 3/1996 | Horng |
| 5,521,357 A | 5/1996 | Lock et al. |
| 5,522,008 A | 5/1996 | Bernard |
| 5,547,616 A | 8/1996 | Dancs et al. |
| 5,556,192 A | 9/1996 | Wang |
| 5,567,361 A | 10/1996 | Harper |
| 5,574,821 A | 11/1996 | Babasade |
| 5,575,992 A | 11/1996 | Kunze |
| 5,577,156 A | 11/1996 | Costello |
| 5,591,395 A | 1/1997 | Schroeder et al. |
| 5,624,230 A | 4/1997 | Taylor et al. |
| 5,634,806 A | 6/1997 | Hahn |
| 5,647,052 A | 7/1997 | Patel et al. |
| 5,647,053 A | 7/1997 | Schroeder et al. |
| 5,651,942 A | 7/1997 | Christensen |
| 5,662,835 A | 9/1997 | Collingwood |
| 5,664,958 A | 9/1997 | Chadwick et al. |
| 5,700,430 A | 12/1997 | Bonnema et al. |
| 5,735,460 A | 4/1998 | Eisenbraun |
| 5,749,520 A | 5/1998 | Martin et al. |
| 5,750,498 A | 5/1998 | Soeda et al. |
| 5,765,751 A | 6/1998 | Joshi |
| 5,788,155 A | 8/1998 | Martin et al. |
| 5,788,931 A | 8/1998 | Munoz Quintana |
| 5,796,914 A | 8/1998 | Gatzemeyer et al. |
| 5,805,768 A | 9/1998 | Schwartz et al. |

| | | |
|---|---|---|
| 5,810,265 A | 9/1998 | Cornelius et al. |
| 5,813,873 A | 9/1998 | McBain et al. |
| 5,832,648 A | 11/1998 | Malone |
| 5,873,529 A | 2/1999 | Johnson |
| 5,875,968 A | 3/1999 | Miller et al. |
| 5,884,808 A | 3/1999 | Muderlak et al. |
| 5,899,381 A | 5/1999 | Gordon et al. |
| 5,903,710 A | 5/1999 | Wefler et al. |
| 5,926,614 A | 7/1999 | Steinel |
| 5,928,605 A | 7/1999 | Bonnema et al. |
| 5,932,204 A | 8/1999 | Joshi |
| 5,937,140 A | 8/1999 | Leonard et al. |
| 5,940,577 A | 8/1999 | Steinel |
| 5,944,223 A | 8/1999 | Klima et al. |
| 5,945,094 A | 8/1999 | Martin et al. |
| 5,955,701 A | 9/1999 | Schockner et al. |
| 5,957,701 A | 9/1999 | McMillin |
| 5,970,643 A | 10/1999 | Gawel, Jr. |
| 5,976,503 A | 11/1999 | Martin et al. |
| 5,998,735 A | 12/1999 | Patterson, Jr. |
| 6,021,254 A | 2/2000 | Hunter |
| 6,031,967 A | 2/2000 | Flashinski et al. |
| 6,032,930 A | 3/2000 | Calino |
| 6,036,536 A | 3/2000 | Chiu |
| 6,044,202 A | 3/2000 | Junkel |
| 6,045,374 A | 4/2000 | Candeloro |
| 6,050,551 A | 4/2000 | Anderson |
| 6,051,788 A | 4/2000 | Nichols |
| 6,078,728 A | 6/2000 | O'Rourke et al. |
| 6,085,026 A | 7/2000 | Hammons et al. |
| 6,097,881 A | 8/2000 | DeWitt et al. |
| 6,099,137 A | 8/2000 | McCormick et al. |
| 6,101,315 A | 8/2000 | Steinel, Jr. |
| 6,104,866 A | 8/2000 | DeWitt et al. |
| 6,104,867 A | 8/2000 | Stathakis et al. |
| D430,659 S | 9/2000 | Zaraboza et al. |
| 6,123,935 A | 9/2000 | Wefler et al. |
| 6,141,496 A | 10/2000 | Sundberg et al. |
| 6,148,143 A | 11/2000 | Steinel, Jr. |
| 6,156,088 A | 12/2000 | Cardarelli |
| 6,197,262 B1 | 3/2001 | Del Ben |
| 6,197,263 B1 | 3/2001 | Blount |
| 6,227,118 B1 | 5/2001 | Nance |
| 6,236,807 B1 | 5/2001 | Ruffolo et al. |
| 6,249,645 B1 | 6/2001 | Smith |
| 6,254,065 B1 | 7/2001 | Ehrensperger et al. |
| 6,264,548 B1 | 7/2001 | Payne, Jr. et al. |
| 6,269,979 B1 | 8/2001 | Dumont |
| 6,270,720 B1 | 8/2001 | Mandish |
| 6,275,651 B1 | 8/2001 | Voit |
| 6,278,840 B1 | 8/2001 | Basaganas Millan |
| 6,285,830 B1 | 9/2001 | Basaganas Millan |
| 6,289,176 B1 | 9/2001 | Martter et al. |
| 6,302,559 B1 | 10/2001 | Warren |
| 6,315,959 B2 | 11/2001 | Mandish |
| 6,328,791 B1 | 12/2001 | Pillion et al. |
| 6,342,676 B1 | 1/2002 | Ha |
| 6,349,168 B1 | 2/2002 | Jaworski |
| 6,352,210 B1 | 3/2002 | Requejo |
| 6,354,513 B1 | 3/2002 | Basaganas Millan |
| 6,361,752 B1 | 3/2002 | Demarest et al. |
| 6,364,673 B1 | 4/2002 | Lee |
| 6,368,564 B1 | 4/2002 | Smith |
| 6,371,815 B1 | 4/2002 | Wetzel et al. |
| 6,374,044 B1 | 4/2002 | Freidel |
| 6,374,045 B2 | 4/2002 | Basaganas Millan |
| 6,381,408 B1 | 4/2002 | Jaworski et al. |
| 6,603,924 B2 | 8/2003 | Brown et al. |
| 6,714,725 B2 | 3/2004 | Grone et al. |
| 2001/0031225 A1 | 10/2001 | Mandish |
| 2001/0053283 A1 | 12/2001 | Levine et al. |
| 2002/0144992 A1 | 10/2002 | Vieira |
| 2003/0138241 A1 | 7/2003 | Ambrosi et al. |

OTHER PUBLICATIONS

PCT International Search Report issued Apr. 21, 2004 for International Application No. PCT/US03/26754, International Filing Date Aug. 28, 2003, 4 pages.

PCT International Search Report issued Nov. 12, 2003 for International Application No. PCT/US03/25245, International Filing Date Aug. 13, 2003, 4 pages.

PCT International Search Report issued Oct. 7, 2003 for International Application No. PCT/US03/04082, International Filing Date Feb. 12, 2003, 8 pages.

PCT International Search Report issued Dec. 16, 2003 for International Application No. PCT/US03/25244, International Filing Date Aug. 13, 2003, 3 pages.

PCT International Search Report issued Dec. 16, 2003 for International Application No. PCT/US03/25246, International Filing Date Aug. 13, 2003, 3 pages.

PCT International Search Report issued Dec. 19, 2003 for International Application No. PCT/US03/25243, International Filing Date Aug. 13, 2003, 4 pages.

Brochure–"Decora Devices," by Leviton, date unknown, Section A, pps. A1–A36.

PCT Written Opinion issued Sep. 17, 2004 for International Application No. PCT/US03/25243, International Filing Date Aug. 13, 2003, 4 pages.

* cited by examiner

VAPOR DISPENSING DEVICE HAVING IMPROVED TRANSVERSE LOADING STABILITY

CROSS-REFERENCE TO RELATED APPLICATIONS

This application is a continuation-in-part of U.S. patent application Ser. No. 10/222,070 entitled "Vapor Dispensing Device Having Improved Transverse Loading Stability" filed Aug. 16, 2002.

FIELD OF INVENTION

This invention generally relates to vapor dispensing devices such as air fresheners. More particularly, the invention relates to electrically-powered vapor dispensing devices.

BACKGROUND OF THE INVENTION

Electrically-operated vapor dispensing devices have been used for several years and have become common household products. These devices are typically inserted into a conventional electrical receptacle to obtain electricity for heating a perfumed fluid, wax, paraffin, or other fuel to produce a pleasing aroma that is dispersed within a room or other confined space. Examples of electric vapor dispensers include the RENUZIT products available from The Dial Corporation of Scottsdale, Ariz. One such product is shown in U.S. Design Pat. Ser. No. D449,101 which issued on Oct. 9, 2001 to Wolpert et al.

Many conventional vapor dispensing devices exhibit a marked disadvantage, however, in that the size of the dispenser housing frequently extends outwardly from the wall receptacle for a significant distance. Because of this distance, an outcropping from the wall is produced that can become bumped, jostled or otherwise accidentally placed into contact with people or objects. Such contact may have the effect of pushing the dispenser out of the wall receptacle, and may potentially break or deform the device. Accordingly, it is desirable to produce an electric vapor dispenser that is resilient to accidental contact that may produce breakage or displacement of the dispenser.

SUMMARY OF THE INVENTION

A vapor dispensing device having a high transverse loading stability is provided in accordance with various embodiments of the invention. Such a device includes a relatively low profile with respect to the supporting wall or electrical receptacle such that the frequency and impact of accidental physical contact with the device are appropriately reduced. According to an exemplary embodiment, the housing of a vapor dispensing device is designed such that the perpendicular distance from the outlet face of the wall receptacle to a worst-case transverse loading point ($d_L$) is less than the distance from the plug to a worst-case support point ($d_S$) such that a transverse loading coefficient $\eta = d_S/d_L$ is greater than one. These and other aspects of the invention shall become more apparent when read in conjunction with the accompanying drawing figures and the attached detailed description of exemplary embodiments.

BRIEF DESCRIPTION OF THE DRAWING FIGURES

The features and advantages of the present invention are hereinafter described in the following detailed description of exemplary embodiments to be read in conjunction with the accompanying drawing figures, wherein like reference numerals are used to identify the same or similar parts in the similar views, and.

DETAILED DESCRIPTION OF EXEMPLARY EMBODIMENTS

Figure 1:
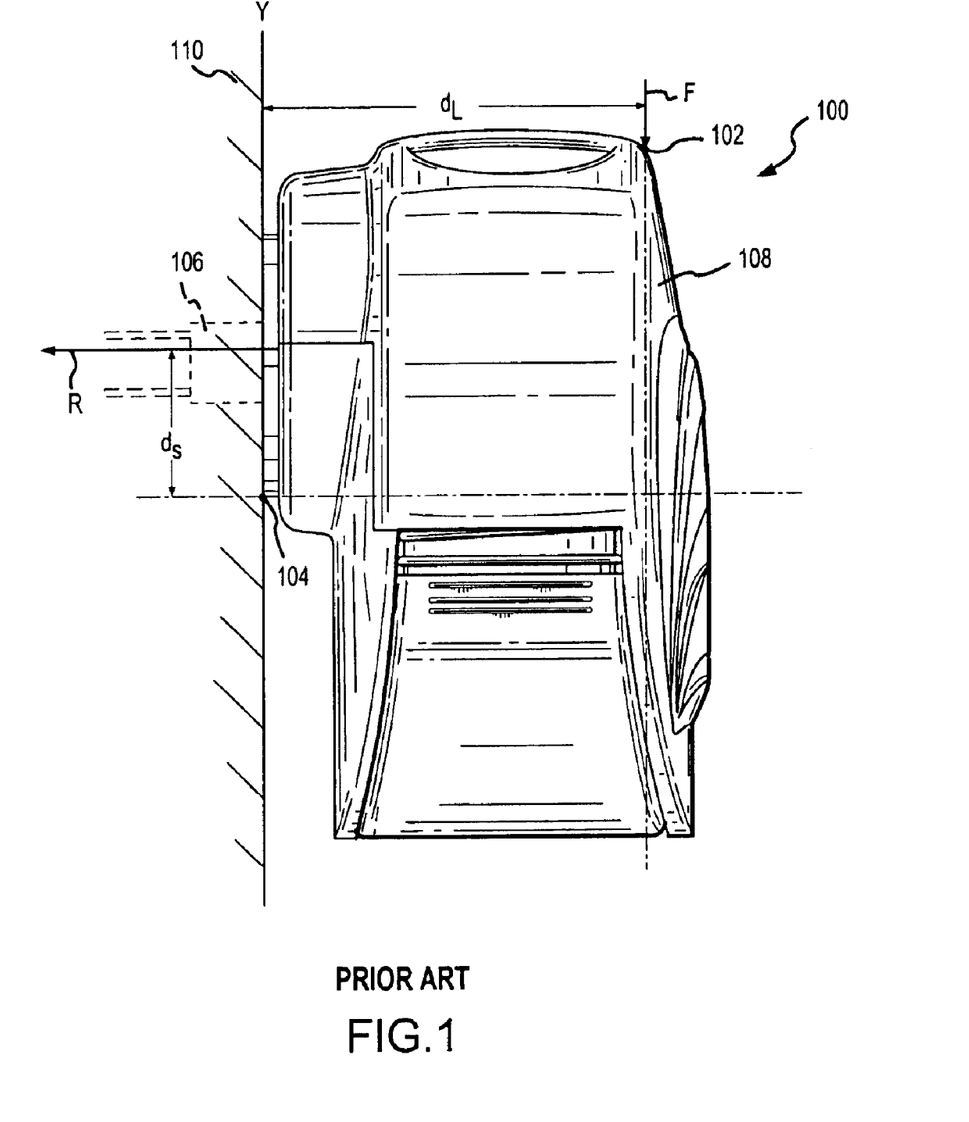
FIG. 1 is a side view of a conventional vapor dispensing device.

With reference to FIG. 1, a conventional vapor dispensing device 100 typically includes a housing 108 coupled to a plug 106 that is capable of being inserted into a conventional electrical receptacle in a wall or other structure 110. Housing 108 typically retains a vapor-producing material such as a perfumed fluid, wax, paraffin or the like that can be combusted, electrolyzed or otherwise processed by a resistance heater or other appropriate device to produce a vapor that can be dispersed through a room, vehicle or other confined space.

Due to the relatively large profile of vapor dispensing device 100 with respect to wall 110, however, forces impacting on the vapor dispensing device 100 suitably produce rotational moments about a support point along the wall. For example, force F applied at point 102 on housing 108 suitably produces a rotational moment about point 104 that is equal to the magnitude of force F multiplied by the distance $d_L$ from the effective point of force F to the front face of the outlet. This loading distance $d_L$ is defined as the distance from the effective point of force F from an axis that is perpendicular to the front face of the outlet and that runs through a support point 104. In the vapor-dispensing device 100 shown in FIG. 1, support point 104 is the point on device 100 that bears the greatest impact of force F.

Application of force F produces a reactive force R between plug 106 and wall 110. Reactive force R appropriately maintains vapor-producing device 100 in contact with the outlet receptacle, and produces a counter-balancing rotational moment upon support point 104. The moment produced by the stabilizing force R about support point 104 is equal to the magnitude of reactive force R multiplied by the distance from force R to support point 104. This distance is referred to herein as support distance $d_S$ and is typically measured along an axis parallel to the outlet face. Because vapor dispensing device 100 remains rigidly fixed in position and does not move in response to the application of force F, the sum of the moments about point 104 suitably equates to zero. The sum of the moments about point 104 may therefore be expressed as:

$$R\, d_S - F\, d_L = 0 \qquad \text{(Equation 1)}$$

Manipulating these terms algebraically shows that the resulting force R produced into the wall by force F is as follows:

$$R = F\frac{d_L}{d_S} = \frac{F}{\eta} \quad \text{(Equation 2)}$$

wherein η is a transverse loading coefficient defined as the ratio of the support distance $d_S$ to the load distance $d_L$. In vapor dispensing device 100 shown in FIG. 1, it is clear that lateral distance $d_L$ is relatively large compared to $d_S$, thereby indicating that the transverse loading coefficient η is less than 1. Accordingly, it can be readily shown from Equation 2 that a load force F upon point 102 effectively produces a resultant force R that has a greater magnitude than that of force F when the transverse loading coefficient η is less than one.

Figure 2:
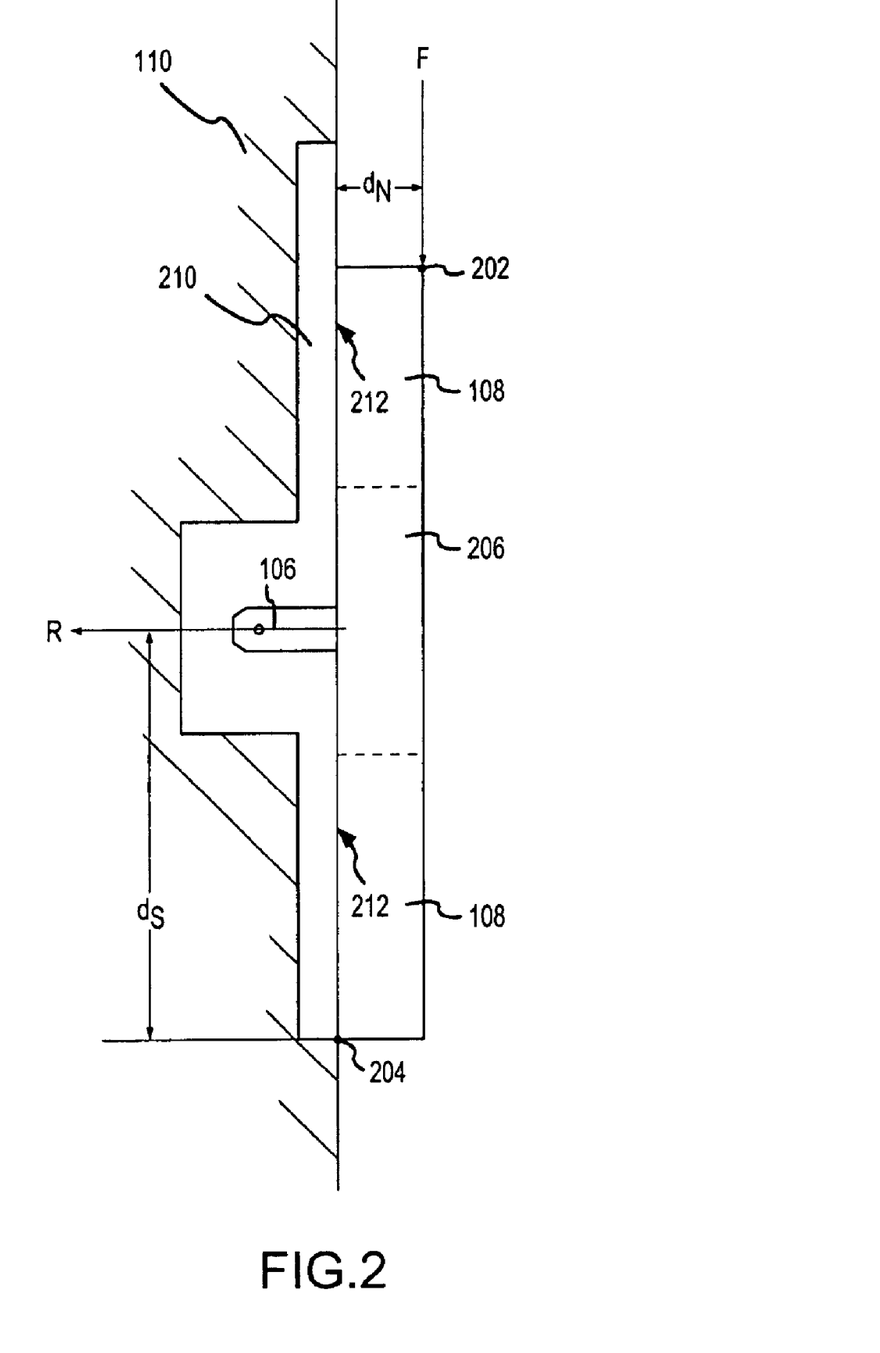
FIG. 2 is a side view of an exemplary vapor dispensing device with a high transverse loading stability.

FIG. 2 is a side view of a vapor dispensing device having an improved transverse loading stability. With reference now to FIG. 2, a vapor dispensing device 200 suitably includes a housing 108 coupled to a plug 106 that is capable of being inserted into the outlet face 212 of a conventional electrical receptacle 210 housed in a wall or other surface 110. Housing 108 may also include a conventional device outlet 206 electrically coupled to the plug that provides electrical power from plug 106 to a light or other electrically-powered device such as a hairdryer, curling iron, electric razor, kitchen appliance, or the like.

FIG. 2 depicts a force F impinging upon a worst-case transverse loading point 202 along housing 108. Worst-case loading point 202 is any point along the edge of device 200 that is furthest from the outer face 212 of the electrical receptacle. Worst-case loading point 202 corresponds to locations on housing 108 where the impinging force produces a maximum rotational moment about a worst-case support point 204, which is defined as the points on housing 108 wherein the moment produced by reactive force R is maximized. Worst-case support points 204 typically reside on an edge of housing 108 that is in physical contact with the front face of the receptacle and that is on a side of housing 108 opposite plug 106 from the impinging point of the force F. Accordingly, device 200 may exhibit multiple worst-case support points along an edge of housing 108 that provide equal reactive moments to external forces. Similarly, forces impinging upon each point along certain edges of housing 108 may produce identical moments in the various support points. Accordingly, the precise locations of worst-case loading and support points on device 400 vary widely depending upon the particular embodiment and forces applied.

In the device shown in FIG. 2, worst-case support point 204 is defined near the bottom of vapor dispensing device 200 at the point on housing 108 that bears the greatest loads from applied external forces. Worst-case transverse loading point 202 corresponds to the point on vapor dispensing device 200 whereupon application of a force F produces the greatest resultant force R between plug 106 and the surrounding receptacle 210. Using Equation 2 above, the resultant force R is:

$$R = F\ d_L/d_S = \frac{F}{\eta}$$

In this case, however, the transverse loading coefficient η is greater than one because support distance $d_S$ from plug 106 to support point 204 along outlet face 212 is designed to be greater than the lateral distance $d_L$ from outlet face 212 to loading point 202. Correspondingly, then, force F applied at worst-case transverse loading point 202 produces a resulting force R with a magnitude that is less than the magnitude of force F, thereby reducing the impact of force F on plug 106 and improving the overall transverse loading stability of vapor dispensing device 200.

Figure 3:
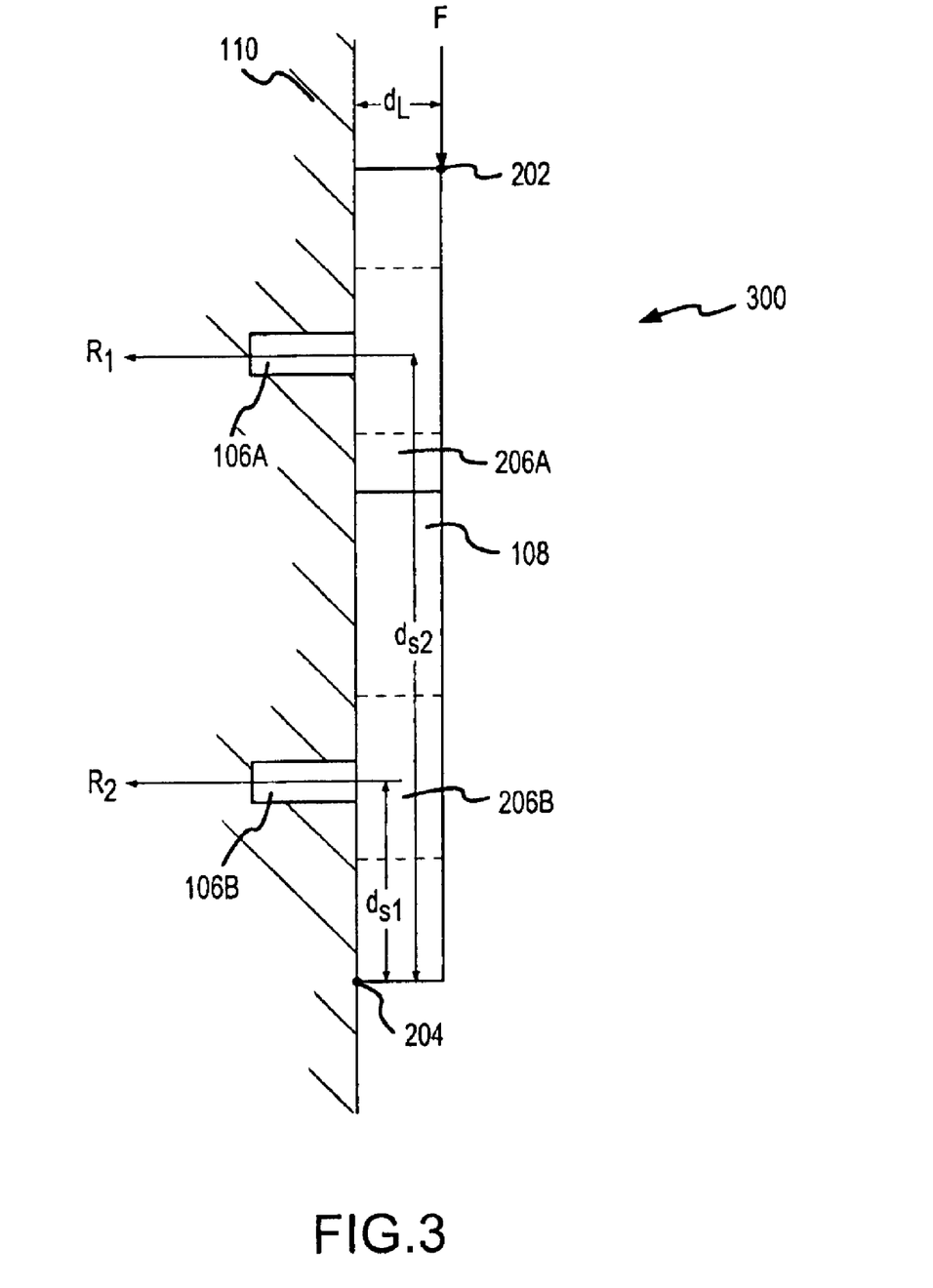
FIG. 3 is a side view of an exemplary vapor dispensing device having two plugs and a high transverse loading stability.

FIG. 3 is a side view of a vapor dispensing device having more than one plug which can be inserted into an electrical receptacle. With reference now to FIG. 3, a vapor dispensing device 300 suitably includes housing 108 coupled to two plugs 106a and 106b. Either or both of the plugs 106a–b may be an electrical communication with one or more device outlets 206 to provide electrical power from receptacle 210 (FIG. 2) to external devices such as lamps, hair dryers or the like.

In the embodiment shown, the worst-case transverse loading point remains at point 202, which is the greatest perpendicular distance $d_L$ from the face of the outlet. Similarly, worst-case support point 204 remains at the edge of housing 108 at a distance furthest from plugs 106A–B and opposite worst-case transverse loading point 202. Because two plugs 106A–B are provided, two resultant forces $R_1$ and $R_2$ are produced. Accordingly, the rotational moments about point 204 are appropriately expressed as:

$$R_1\ d_{S2} + R_2\ d_{S1} - F\ d_L = 0. \quad \text{(Equation 3)}$$

Algebraically manipulating Equation 3 results in:

$$F = R_1\ d_{S1}/d_L + R_2\ d_{S2}/d_L = R_1\eta_1 + R_2\eta_2 \quad \text{(Equation 4)}$$

wherein $\eta_1 = d_{S1}/d_L$ and $\eta_2 = d_{S2}/d_L$. Evaluating Equation 4 shows that force F applied at point 202 is appropriately counterbalanced by two resultant forces $R_1$ and $R_2$. In each case, the transverse loading coefficients $\eta_1$ and $\eta_2$ are designed to be greater than one such that the support distance $d_S$ is greater than the loading distance $d_L$ for each plug 106A–B. Because $R_1$ and $R_2$ are inversely proportional to $\eta_1$ and $\eta_2$, respectively, it may be readily shown that relatively large values for $\eta_1$ and $\eta_2$ result in correspondingly smaller reactive forces $R_1$ and $R_2$ for a constant value of F. Further, because unusually high values of $R_1$ and $R_2$ can cause breakage or movement of device 300, higher values for $\eta_1$ and $\eta_2$ thereby allow device 300 to produce lower reactive forces and to thereby withstand greater forces F without breakage or movement. Accordingly, the transverse loading stability of device 300 is improved.

FIGS. 4A–D are top, front, side and perspective views, respectively, of another exemplary embodiment of a vapor-dispensing device. With reference to FIGS. 4A–D, vapor dispensing device 400 suitably includes a housing 108 connecting to one or more plugs 106A–B. Housing 108 and plugs 106A–B are appropriately configured to correspond with the front face 212 of a wall-mounted outlet receptacle 210 (FIG. 4D) to provide device stability and electrical power.

Figure 4A:
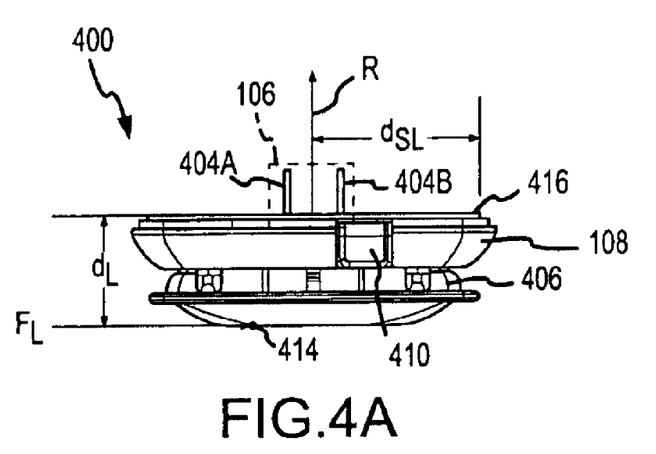
FIGS. 4A–D are top, front, side and perspective views, respectively, of an exemplary vapor dispensing device having a high transverse loading stability.
Figure 4B:
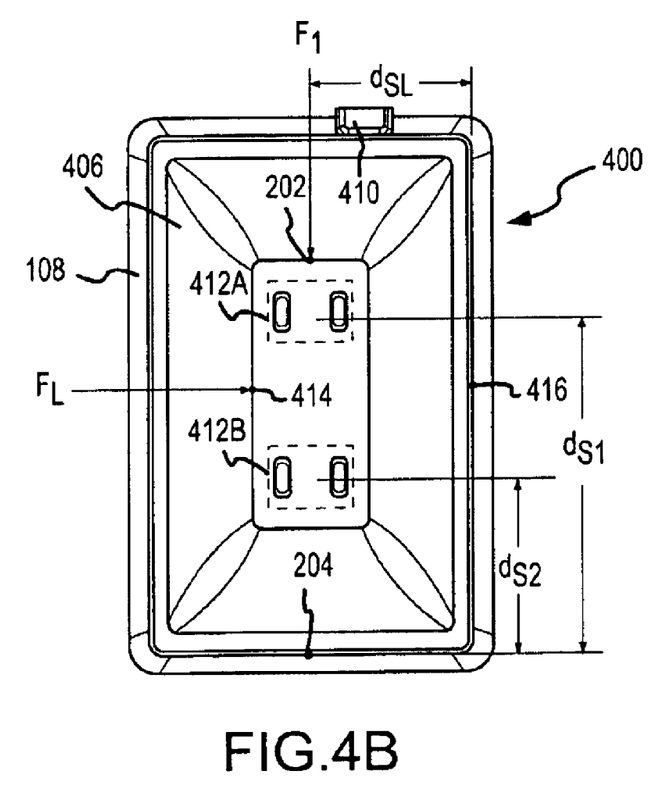

In the exemplary embodiment shown in the drawings, housing 108 suitably includes two optional device outlets 412A–B that allow the user to connect other appliances to plugs 106A–B to obtain electrical power while device 400 remains in use. Each of the plugs 106A–B has two prongs 404A–B as best seen in FIG. 4A. To simplify the discussion below, however, the reactive forces produced by each prong 404A–B are analyzed as a combined reactive force R for the entire plug 106. Plug 106 may conform to any electrical convention such as the 60 Hertz, 110 Volt alternating-current standard commonly used in North America. Alternatively, plug 106 may be configured to operate using direct current (e.g. current supplied by a battery) or any other electrical convention.

Fragrance is produced in device 400 by any conventional technique and structure. In an exemplary embodiment, device 400 suitably uses electrical resistance to heat a fragrance-producing fuel such as a perfumed fluid, wax or other substance maintained in a reservoir within or coupled to housing 108. In a further exemplary embodiment, device 400 suitably interfaces to an optional replaceable fragrance cartridge (or "refill component") 406 to replenish the supply of fuel as needed. The cartridge may be discarded and replaced when the fuel is spent, when the user desires an alternate fragrance or as otherwise appropriate. An optional flat lamp, night light or other lighting feature may also be provided within fragrance-producing device 400. The term "housing" as used herein is intended to broadly include features such as removable cartridges, lamps and the like that may be coupled or otherwise attached to device 400.

Housing 108 may also include or interface with an optional fragrance intensity slider 410. Slider 410 allows users to adjust the intensity of fragrance produced by device 400 by moving slider 410 to a desired linear position corresponding to the rate by which fragrance is allowed to diffuse or move into the surrounding space. Alternate embodiments may use a rotary dial, switch or other control in place of slider 410 to adjust the fragrance intensity, or may eliminate fragrance intensity adjustment altogether.

Figure 4C:
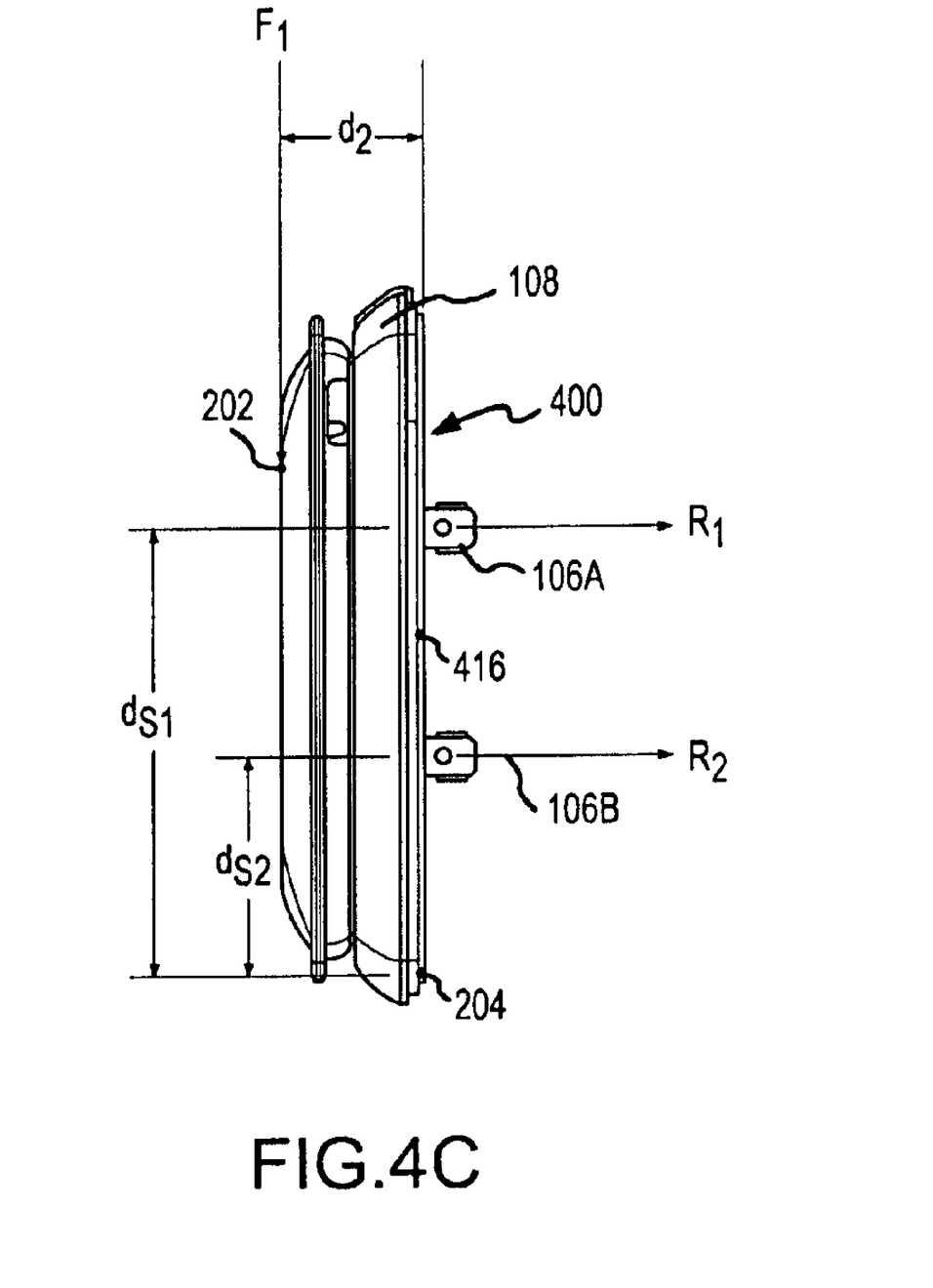
Figure 4D:
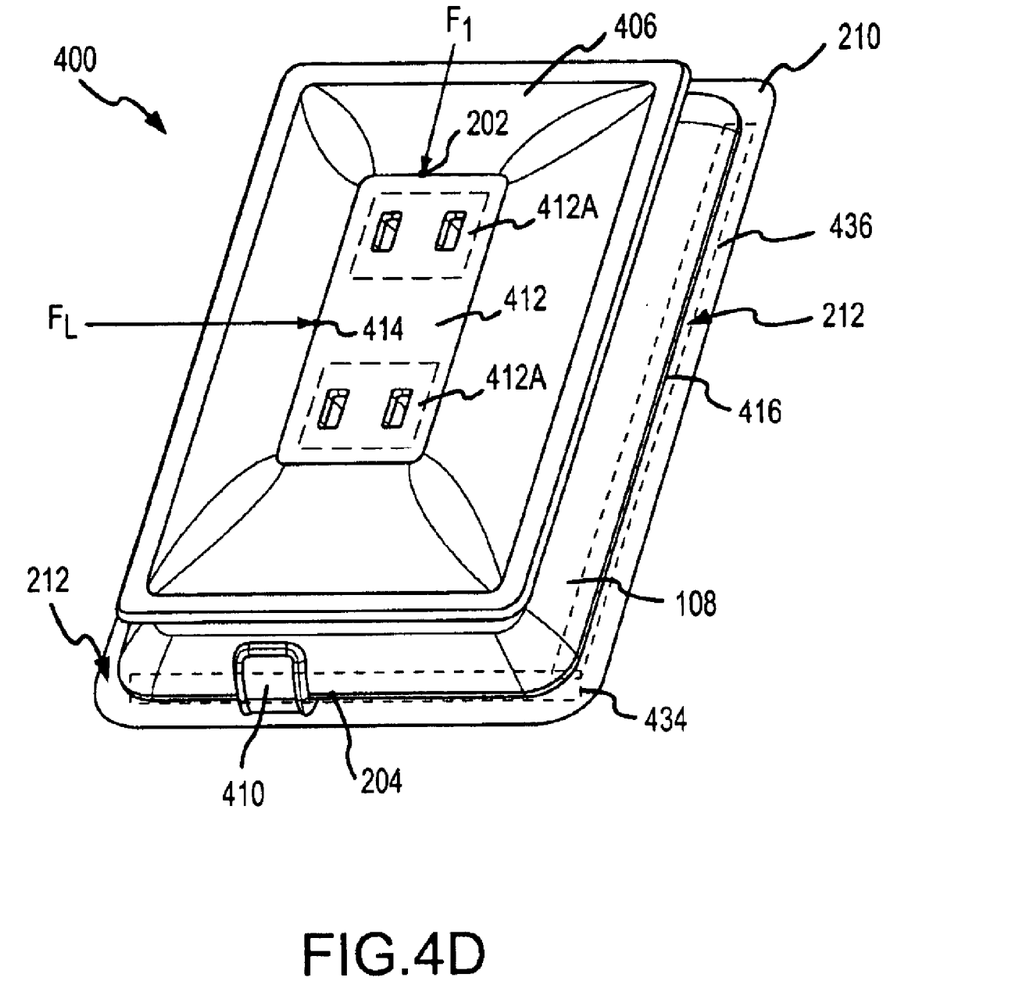

FIGS. 4A–D depict two separate forces $F_1$ and $F_L$ impinging upon worst-case transverse loading points 202 and 414, respectively. Worst-case loading points 202 and 414 correspond to locations on housing 108 where the impinging forces $F_1$ and $F_L$ produce maximum rotational moments upon device 400. Accordingly, the worst case loading points on device 400 are the points furthest from the outlet face along outer ridge 432 of device 400 as shown in FIG. 4D.

Worst case support points 204 and 416 lie along the outer edge of housing 108 facing the electrical receptacle and opposite plugs 106A-B, since the rotational moments produced by reactive forces $R_1$ and $R_2$ are maximized along edges 434 and 436 (FIG. 4D), respectively. To simplify discussion, points 204 and 416 are considered as worst case support points for forces $F_1$ and $F_L$, respectively, although other points along edges 434 or 436 would produce similar results.

With continued to FIGS. 4A–D, force $F_1$ is shown applied to worst-case loading point 202, which is located along the upper edge of housing 108 at a point furthest outward from the outlet face. Force $F_1$ is therefore applied a distance of $d_L$ (FIGS. 4A and 4C) from the outlet face to produce a moment of magnitude $F \times d_L$ about worst case support point 204. Plugs 106A and 106B effectively produce reactive forces $R_1$ and $R_2$ at distances $d_{S1}$ and $d_{S2}$ from support point 204, respectively, to generate rotational moments about point 204 equal to $R_1 \times d_{S1}$ and $R_2 \times d_{S2}$, respectively. Applying the analysis of equation 4 set forth above, the transverse loading stability of device 400 is suitably improved by designing distances $d_{S1}$ and $d_{S2}$ to be relatively long compared to distance $d_L$. Stated another way, stability is improved by designing the maximum thickness of device 400 to be less than the shortest distance from either plug 106A-B to any loading edge (e.g. edges 434 and 436) of housing 108 that is in contact with outlet face 212.

Similarly, force $F_L$ is shown applied to worst-case loading point 414, which (like point 202) is located along the upper edge of housing 108 at a point furthest outward from the outlet face. Force $F_L$ is therefore applied a distance of $d_L$ (FIGS. 4A and 4C) from the outlet face to produce a moment of magnitude $F_L \times d_L$ about worst case support point 204, which lies along edge 436 as described above. Plugs 106A and 106B effectively produce reactive forces $R_1$ and $R_2$ at a distance $d_{SL}$ from support point 204. In this case, $R_1$ and $R_2$ are produced at an equal distance from support point 204 along an axis parallel to the outlet face as best seen in FIG. 4C. Accordingly, $R_1$ and $R_2$ generate rotational moments about point 204 with magnitudes equal to $R_1 \times d_{SL}$ and $R_2 \times d_{SL}$, respectively. Again applying the analysis of equation 4 set forth above, the transverse loading stability of device 400 is suitably improved by designing distance $d_{SL}$ to be relatively long compared to distance $d_L$.

Regardless of the type of volatizable material used, the material delivery system may employ any form of controller to modulate the delivery of vapor into the environment. To the extent that the rate at which the vapor is introduced into the environment is a function of both the temperature of the volatizable material and the environmental convection conditions in the vicinity of the volatizable material, any suitable control mechanism may be employed to modulate these two factors. For example, the convection conditions may be controlled through the use of adjustable convection inhibitors (e.g., one or more vents) one or more convection enhancers (e.g., fans, chimney structures, etc.), or other structures that modify the vapor pressure in and around the material delivery system. Similarly, the temperature of the volatizable material and/or the temperature of the environment in the vicinity of the material delivery system may be controlled through any convenient method, including resistive heating (described above), or through proximity of the device to a preexisting heat source.

Notwithstanding the nature of receptacle 210—i.e., whether and to what extent the receptacle is configured to supply electrical current—the device may be passive, active, or selectably switched between active and passive modes. The term "passive" in this context, as applied to delivery devices, refers to those devices which substantially depend upon ambient conditions to deliver a fragrance or otherwise give rise to a modification of the environment. Such ambient conditions include, for example, ambient thermal conditions (e.g., wall surface temperature and air temperature) and ambient air flow, (e.g., air flow resulting from free convection as well as the movement (if any) of fans, individuals, and other entities within the environment). The term "active" in this context refers to devices that are not passive, e.g., devices which employ integrated fans, heating elements, and other such devices.

In the event that the vapor dispensing device is an active device, any power source required by the device may be intrinsic to receptacle 210, e.g., the 120 V source of a standard wall outlet, or extrinsic to receptacle 210, e.g., supplied by a battery, solar cell, or other such device incorporated into or otherwise associated with delivery device 100. Alternatively, power may be supplied by a combination of intrinsic and extrinsic sources and/or may be incorporated into a refill component.

Delivery device 100 suitably includes one or more removeably attached refill components as briefly mentioned above. That is, referring to FIGS. 5A–5C, it may be advantageous for the delivery device to include components that are integral to housing 108 of the delivery system itself as well as one or more refill components 406 (or simply "refills") that can be replaced by the user. In the event delivery system 100 is an air freshener device, for example, a depleted refill component 406 may removed from system 100 and replaced by a new refill containing fragrant oil, wax, gel, or the like. The refill suitably includes a refill body and a volatizable material provided therein.

In accordance with one aspect of the present invention, a refill component is provided which allows a vapor-dispensing device to mimic an electrical receptacle. For example, a refill component comprising a refill body having a volatizable material provided therein may be configured to be inserted behind the front surface of the device such that it is substantially concealed by the front surface. In accordance with one aspect of the present invention, the refill has a perimeter that is encompassed by the perimeter of the housing.

Figure 5A:
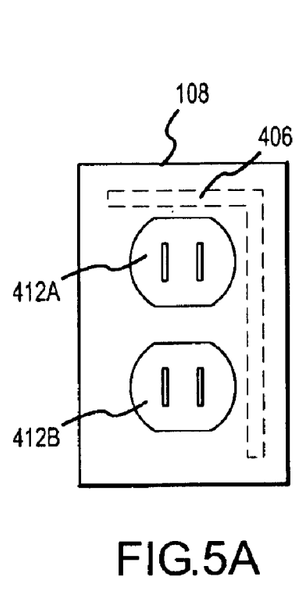
FIGS. 5A–5C depict various refill configurations in accordance with the present invention.
Figure 5B:
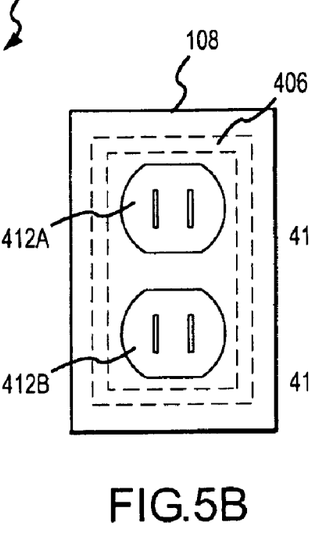
Figure 5C:
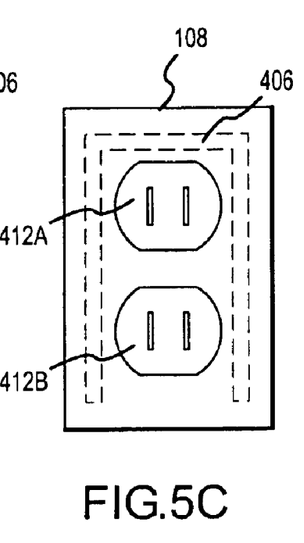

In accordance with another aspect of the present invention, refill 406 is configured such that it does not significantly obstruct the receptacle's outlet pattern (comprising, for example, two outlets 412A and 412B). In one embodiment, for example, this is accomplished by providing a refill component 406 that at least partially surrounds one or more outlets on the receptacle (variously shown in FIGS. 5A–5C). In the event that the delivery device is used in connection with a standard electrical receptacle, it is desirable for refill 406 to encompass two or more sides of the outlet pattern (FIG. 5A). To the extent that it is advantageous to supply the greatest possible volume of volatizable material, the refill may be configured as a rectangular ring that completely surrounds the outlet pattern (FIG. 5B). Alternatively, the refill may be configured in a 'U' shape to allow refill 406 to be slideably removed from the device (FIG. 5C).

For the sake of brevity, conventional electrical and mechanical design techniques used in developing various vapor-dispensing devices (and the various components thereof) are not described in detail herein. Accordingly, devices disclosed herein may be readily modified to create equivalent embodiments through application of general electrical and mechanical principles. Although the embodiments described herein show vapor dispensing devices that are generally quadrilateral in shape, for example, other design styles could be formulated. Vapor dispensing devices could be readily formulated with angular, round, oval or other shapes, for example, as well as with combinations of multiple shapes and structures. In a further embodiment, the vapor dispensing device may be adorned with an ornamental design such as a floral design, an outdoor scene, a cartoon or movie character, or the like. Moreover, the general concepts of improving transverse loading stability described herein may be applied to other electrical devices such as air filters, nightlights, audio speakers, wireless control devices, timers and the like.

The particular implementations shown and described herein are examples of the invention and are not intended to otherwise limit the scope of the invention in any way. The connecting lines shown in the various figures contained herein are intended to represent exemplary functional relationships and/or physical couplings between the various elements. It should be noted that many alternative or additional functional relationships, physical connections or logical connections may be present in a practical vapor-dispensing device. The corresponding structures, materials, acts and equivalents of all elements in the claims below are intended to include any structure, material or acts for performing the functions in combination with other claimed elements as specifically claimed. The scope of the invention should be determined by the appended claims and their legal equivalents, rather than by the examples given above. No item or component is essential to the practice of the invention unless the element is specifically described herein as "critical", "essential" or "required".

What is claimed is:

1. A vapor-dispensing device having a high transverse loading stability when connected to an electrical receptacle having an outlet face, said vapor-dispensing device comprising:

a housing;

a device outlet provided within said housing;

a plug electrically coupled to said device outlet and configured to be inserted into said outlet face;

a vapor delivery device coupled to said housing;

a refill component removeably attached to said vapor delivery device, said refill component including a refill body and a volatizable material provided therein;

said refill component at least partially surrounds the outlet;

said housing having a worst-case transverse loading point a distance $d_L$ from said outlet face along an axis through said worst-case transverse loading point and substantially perpendicular to said outlet face;

said housing having a worst-case support point a distance $d_S$ from said plug along an axis through said worst-case support point and substantially parallel to said outlet face;

said transverse loading stability of said vapor dispensing device characterized by a transverse loading coefficient η, defined as:

$$\eta \equiv d_S/d_L$$

wherein said vapor dispensing device has a transverse loading coefficient η>1.0.

2. The apparatus of claim 1, wherein said refill is generally "U"-shaped.

3. The apparatus of claim 2, wherein said refill is configured to slideably attach to the environment-altering apparatus.

4. The apparatus of claim 1, wherein said refill is a rectangular ring.

5. The apparatus of claim 1, wherein the vapor-delivery device is passive.

6. The apparatus of claim 1, wherein the vapor-delivery device is active.

* * * * *